US00PP30454P2

(12) United States Plant Patent
Hansen

(10) Patent No.: US PP30,454 P2
(45) Date of Patent: Apr. 30, 2019

(54) ***DIANTHUS* PLANT NAMED 'SCARLET FEVER'**

(50) Latin Name: *Dianthus barbatus*
Varietal Denomination: Scarlet Fever

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 15/932,133

(22) Filed: Feb. 7, 2018

(51) Int. Cl.
*A01H 5/02* (2018.01)
*A01H 6/30* (2018.01)

(52) U.S. Cl.
USPC ..... Plt./283
CPC ..... *A01H 6/305* (2018.05)

(58) Field of Classification Search
USPC ..... Plt./272, 283
See application file for complete search history.

*Primary Examiner* — Susan McCormick Ewoldt

(57) ABSTRACT

The new and distinct cultivar of perennial *Dianthus barbatus* plant named 'Scarlet Fever' is characterized by compact clumps with numerous, vertical, densely-branched stems with green foliage developing reddish coloration on over-wintered plants producing a multitude of flowers of bright reddish-orange flowers completely covering the top of the plant. The new plant is useful for the landscape in containers, as specimens, en masse or as a cut flower.

1 Drawing Sheet

Botanical classification: *Dianthus barbatus.*
Variety denomination: 'Scarlet Fever'.

BACKGROUND OF THE INVENTION

The present invention relates to a new and distinct cultivar of *Dianthus* plant, botanically known as *Dianthus barbatus* 'Scarlet Fever' and hereinafter referred to by the cultivar name or as the new plant.

'Scarlet Fever' was discovered by the inventor in a research area at a wholesale perennial nursery in Zeeland, Mich., USA. The new plant was an induced branched sport found the first week of June 2014 on a single plant of *Dianthus* 'Heart Attack' (not patented) treated for ploidy conversion.

Asexual reproduction of *Dianthus* 'Scarlet Fever' by stem cuttings since early summer of 2014 at the same nursery in Zeeland, Mich. has shown that the unique features of the new plant are maintained through multiple generations of asexual propagation. The characteristics of 'Scarlet Fever' have been determined to be stable and are reproduced true to type in successive generations.

No plants of *Dianthus* 'Scarlet Fever' have been sold or disclosed by this or any other name, in this country or anywhere in the world, except that which was either derived directly or indirectly from the inventor and disclosed within one year of the filing of this application.

SUMMARY OF THE INVENTION

Plants of *Dianthus* 'Scarlet Fever' have not been observed under all possible environmental conditions. The phenotype may vary somewhat with variations in environment such as temperature, available water, fertility and light intensity without, however, any variation in genotype.

The following traits have been repeatedly observed and are determined to comprise the unique characteristics of *Dianthus* 'Scarlet Fever' and distinguish it as a new and distinct Sweet William plant unique from all other *Dianthus* plants known to the inventor:

1. Dense branched clumps with vertical stems.
2. Dense, green foliage that exhibits reddish coloration when mature at both basal and apical ends.
3. Large panicles of bright reddish-orange flowers.
4. Overwintering perennial characteristics.

Compared with the sport, 'Heart Attack', the new plant has a different colored flower with a more orangish-red and lighter green foliage. The nearest comparison variety known to the inventor is 'Red Romance'(U.S. Plant Pat. No. 14,249). The new plant is shorter, has denser growth habit compared with 'Red Romance' and may exhibit stronger perennial characteristics rather than biennial or annual.

BRIEF DESCRIPTION OF THE PHOTOGRAPHS

The photograph of the new plant demonstrates the unique traits and the overall appearance of *Dianthus* 'Scarlet Fever'. The colors are as accurate as reasonably possible with color reproductions of this type. Variations in ambient light spectrum, source and direction may cause the appearance of minor variation in color. The plants used in the photograph were two-year-old plants grown in an open, full-sun botanical garden at a nursery in Raleigh, N.C. with supplemental water and fertilizer when needed. No plant growth regulators or pinching have been used.

DETAILED BOTANICAL DESCRIPTION

Figure 1:
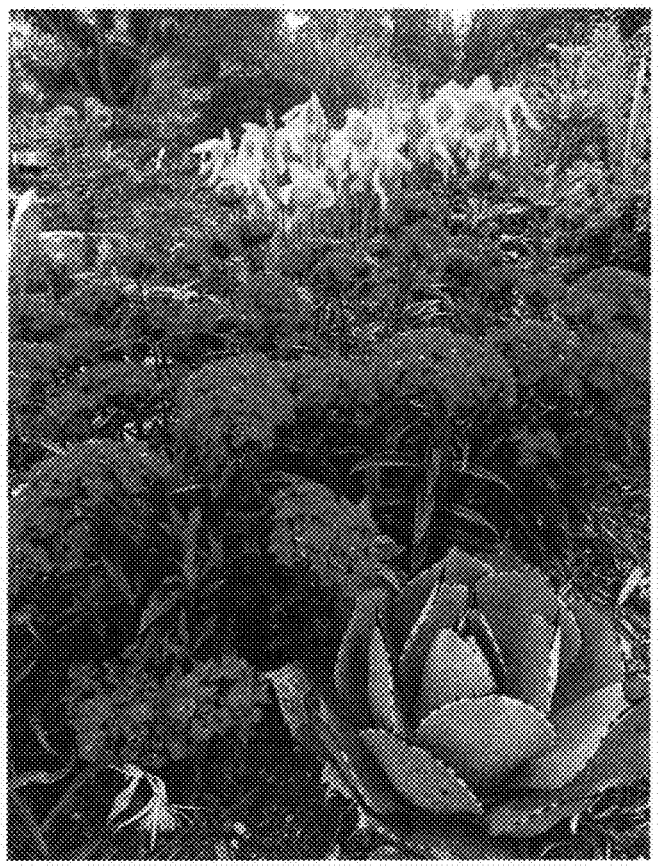
FIG. 1 shows the habit of the new plant in full flower.
Figure 2:
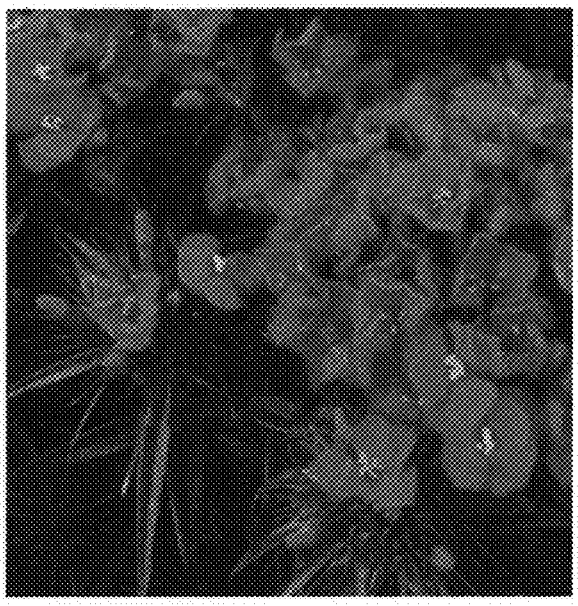
FIG. 2 shows a close-up of the flowers and buds.

The following is a detailed description of two-year-old plants of the new cultivar as grown outdoors in a full sun botanical garden in Raleigh, N.C. and two-year-old plants grown in a greenhouse in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Botanical designation: *Dianthus barbatus;*

Cultivar denomination: 'Scarlet Fever';

Parentage: Induced branch sport of 'Heart Attack';

Asexual propagation: Stem tip cuttings;

Time to initiate roots: About two weeks;

Time to finish in a 3.8 liter flowering container: About 8 weeks in the spring from a vernalized 5.0 cm plug;

Root description: Thin, fibrous; freely branching; color creamy white;

Growth rate: Vigorous;

Plant habit: Multi-stemmed, winter-hardy, herbaceous perennial to biennial; upright mound;

Plant size: Flowering at about 28.0 cm tall and 24.0 cm wide;

Stems: Terete; glabrous; lustrous; strong; stiff; upright; to 22.0 cm long and 4.0 mm diameter on older stems and 2.5 mm diameter on newer branched stems; about 24 to 28 main stems per plant;

Nodes: Basal portion internodes about 3.0 mm apart; just below flowers internodes about 2.0 cm apart; diameter about 4.0 mm in lower portion and 2.5 mm distally;

Node color: Basal portion nearest RHS N186C, distal portion nearest RHS 145A;

Foliage: Simple; opposite; lanceolate; acute apex; base sessile, truncate, clasping; margin entire with microciliolate hairs; not fragrant;

Leaf size: To 11.5 cm long and 17.0 mm wide, average about 10.0 cm long and 15.0 mm wide;

Leaf color: Young abaxial nearest RHS 145B, young adaxial nearest RHS 145A; over-wintered abaxial nearest RHS 146B, over-wintered adaxial between RHS 139A and RHS N137A; over-wintered leaves develop tinting of nearest RHS N186C in base and toward apex;

Veins: Midrib costate abaxial, color nearest RHS 146C; other veins parallel, same color as surrounding tissue abaxial and adaxial;

Petiole: Sessile;

Inflorescence: Compound corymb; about 8.0 cm across and 6.0 cm tall; flowering beginning the last week in May in Zeeland, Mich. and continuing for at least four weeks; about 50 to 80 flowers per compound corymb; self-cleaning; effective for about 3 weeks;

Buds: Clavate, swollen in distal end; to 6.0 mm across in distal end, 4.0 mm diameter in proximal tube and 2.5 cm long;

Bud color: Nearest RHS 46B;

Flower: Single; actinomorphic; salverform; with five petals; lastingness of flower about five days; about 2.0 cm across and about 2.2 cm long;

Flower fragrance: Faintly sweet;

Peduncle: Terete; glabrous; highly branched; to about 5.0 cm long and 3.0 mm diameter at base;

Peduncle color: Nearest RHS 146C with blushing of nearest RHS 183B in regions of high light exposure;

Petals: Typically five; flabellate with claw and limb; glabrous abaxial; adaxial glabrous except puberulent at base of limb; claw glabrous abaxial and adaxial; limb apex rounded; claw base attenuate; limb apex and margin dentate, claw margin entire; limb about 10.0 mm wide and about 8.0 mm long; claw about 10.0 mm long and tapered to about 0.5 mm wide;

Petal color: Adaxial limb between RHS 53A and RHS 53B, abaxial limb nearest RHS 53B; claw nearest RHS 144D in abaxial and adaxial surfaces;

Androecium: Typically ten;

*Filaments*.—About 9.0 mm long and about 0.2 mm diameter; color nearest RHS NN155B.

*Anther*.—Ellipsoidal; dorsifixed; about 1.0 mm long and 0.7 mm across; color nearest RHS 158D.

*Pollen*.—Abundant; color nearest RHS 158D.

Gynoecium: Single with bifid style split just above ovary; about 20.0 mm long.

*Style*.—About 12.0 mm long and 1.0 mm diameter; color nearest RHS NN155B.

*Stigma*.—Puberulent adaxial, glabrous abaxial; about 3.0 mm long; color nearest RHS.

*Ovary*.—Superior; ellipsoidal; about 5.0 mm long and 1.5 mm diameter; color nearest RHS145B.

Calyx: Cylindrical; with five sepals fused in base; glabrous;

Sepals: Five; linear; fused in basal 6.0 mm; acute apex;

Sepal color: Nearest RHS N144D;

Epicalyx: Ten; linear;

Fruit and seed: Not yet observed;

Disease and pest resistance: Plants of 'Scarlet Fever' are more perennial than typical plants of *Dianthus barbatus*. Other pest and disease resistance and tolerance outside that normal for *Dianthus barbatus* has not been tested or observed.

It is claimed:

1. The new and distinct perennial *Dianthus barbatus* plant named 'Scarlet Fever' as herein described and illustrated.

* * * * *